Figure 1:
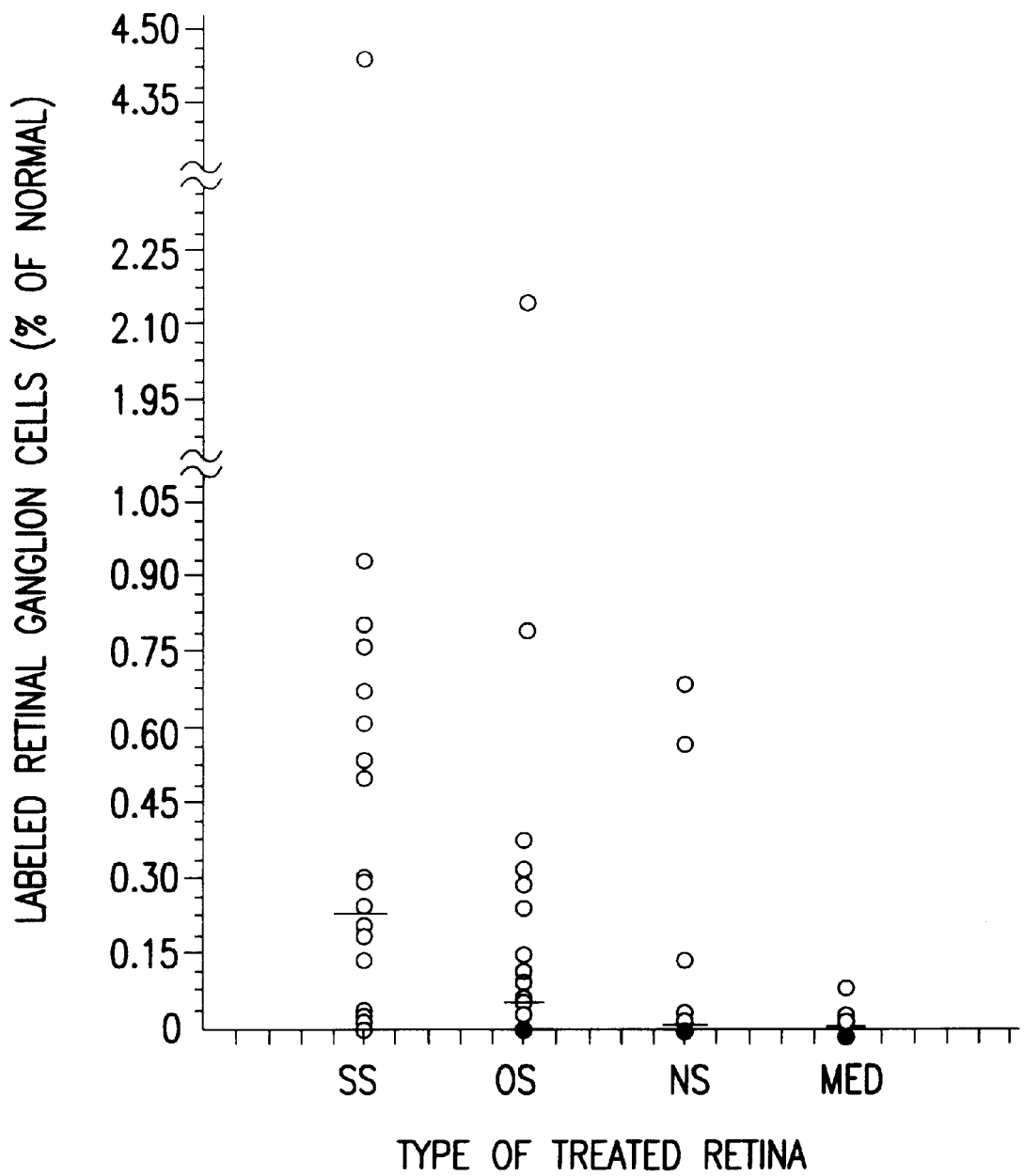

United States Patent [19]
Eisenbach-Schwartz et al.

[11] Patent Number: 6,117,424
[45] Date of Patent: Sep. 12, 2000

[54] COMPOSITIONS OF MONONUCLEAR PHAGOCYTES USEFUL FOR PROMOTING AXONAL REGENERATION

[75] Inventors: Michal Eisenbach-Schwartz; Orly Spiegler, both of Rehovot, Israel; David L. Hirschberg, Stanford, Calif.

[73] Assignee: Yeda Research and Development Co. Ltd., Rehovot, Israel

[21] Appl. No.: 08/818,818

[22] Filed: Mar. 14, 1997

Related U.S. Application Data

[63] Continuation-in-part of application No. 08/695,351, Aug. 9, 1996, Pat. No. 5,800,812, which is a continuation-in-part of application No. 08/528,845, Sep. 15, 1995, abandoned.

[51] Int. Cl.[7] .................................................. A01N 63/00
[52] U.S. Cl. ...................... 424/93.71; 424/93.7; 424/93.1
[58] Field of Search ................................ 424/93.7, 93.71, 424/93.1; 530/325, 355, 372

[56] References Cited

U.S. PATENT DOCUMENTS

| | | |
|---|---|---|
| 5,078,996 | 1/1992 | Conlon, III et al. . |
| 5,082,670 | 1/1992 | Gage et al. . |
| 5,157,024 | 10/1992 | Gordon . |

FOREIGN PATENT DOCUMENTS

| | | |
|---|---|---|
| 0 172 987 A2 | 3/1986 | European Pat. Off. . |
| 0 415 321 A1 | 3/1991 | European Pat. Off. . |
| 0 501 445 A1 | 9/1992 | European Pat. Off. . |

*Primary Examiner*—Patricia A. Duffy
*Attorney, Agent, or Firm*—Pennie & Edmonds LLP

[57] ABSTRACT

Methods and compositions for the use of allogeneic mononuclear phagocytes to promote axonal regeneration in the central nervous system of a mammal are disclosed. In one embodiment, allogeneic mononuclear phagocytes are cultured together with stimulatory tissue, such as dermis or at least one nerve segment, and are subsequently administered into the central nervous system of a mammal at or near a site of injury or disease. In an alternative embodiment, autologous monocytes, preferably stimulated autologous monocytes, are administered into the central nervous system of a mammal at or near a site of injury or disease. Methods for identifying stimulatory tissue and cells and methods and compositions for cryopreserved allogeneic mononuclear phagocytes are also disclosed.

22 Claims, 14 Drawing Sheets

FIG.3A
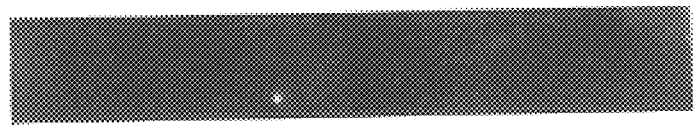
50μm
FIG.3B

COMPOSITIONS OF MONONUCLEAR PHAGOCYTES USEFUL FOR PROMOTING AXONAL REGENERATION

This is a continuation-in-part of co-pending application Ser. No. 08/695,351, filed Aug. 9, 1996 (now U.S. Pat. No. 5,800,812), which is a continuation-in-part of co-pending application Ser. No. 08/528,845, filed Sep. 15, 1995 (now abandoned), each of which is incorporated herein by reference in its entirety.

1. FIELD OF THE INVENTION

The present invention relates to compositions comprising mononuclear phagocytes, and to methods for using mononuclear phagocytes, to promote axonal regeneration in mammals affected by injury or disease of the central nervous system, as well as to compositions and methods for enhancing the therapeutic capacity of mononuclear phagocytes to promote axonal regeneration. In particular, the invention relates to (a) pharmaceutical compositions comprising, and methods for administering, stimulated or non-stimulated allogeneic mononuclear phagocytes at or near a site of the mammalian central nervous system affected by injury or disease to promote axonal regeneration, (b) compositions and methods for stimulating mononuclear phagocytes so as to enhance their capacity to promote axonal regeneration, and (c) methods for screening tissues, cells, proteins, peptides and other biologically active agents for their ability to stimulate mononuclear phagocytes for promoting axonal regeneration.

2. BACKGROUND OF THE INVENTION

Following axonal injury, neurons of the mammalian central nervous system (CNS) have a poor capacity for axonal regeneration. By contrast, neurons of the mammalian peripheral nervous system (PNS) have a substantially greater capacity for axonal regeneration. See Schwartz et al., 1989, FASEB J. 3:2371–2378.

The difference between axonal regeneration in the CNS and PNS has been attributed to the cellular environment of the neurons rather than to the neurons themselves. Following neuronal injury, the Schwann cells that surround PNS neurons are modulated so as to become permissive or supportive for axonal regeneration. By contrast, the astrocytes, oligodendrocytes and microglia that surround CNS neurons do not show such modulation and remain unsupportive or inhibitory for axonal regeneration. See Schwartz et al., 1987, CRC Crit. Rev. Biochem. 22:89–110.

This lack of modulation has been correlated with differences in the post-injury inflammatory response. See Perry and Brown, 1992, Bioessays 14:401–406; Lotan and Schwartz, 1994, FASEB J. 8:1026–1033. In particular, the accumulation of mononuclear phagocytes in response to CNS injury is delayed and limited in comparison with the response to injury in the PNS. This limited CNS mononuclear phagocyte response may in turn lead to (1) inefficient removal of the myelin debris that reportedly inhibits axonal regeneration, and (2) suboptimal release of macrophage-derived cytokines that would promote modulation of astrocytes and oligodendrocytes so as to support axonal regeneration.

The above observations have prompted speculation that appropriate modulation of the macrophage response might promote axonal regeneration after CNS injury. In an in vitro system, David et al. showed that when cryostat sections of normal rat optic nerve are co-cultured with mononuclear phagocytes derived from lesions of the rat CNS, the optic nerve sections show enhanced adhesiveness for embryonic chick dorsal root ganglion cells. David et al., 1990, Neuron 5:463–469. Conditioned medium from activated peritoneal macrophages was also effective in promoting adhesiveness of optic nerve sections in this in vitro assay.

However, results derived from in vivo models of CNS injury have revealed that some interventions that enhance the macrophage response to CNS injury do not result in enhanced regeneration. For instance, local injection of either tumor necrosis factor alpha (TNF-α) or colony stimulating factor-1 (CSF-1) enhanced the macrophage response to experimental optic nerve injury. However, only TNF-α, but not CSF-1, increased the permissiveness of the injured optic nerves for neuronal adhesion as assayed in vitro. Lotan et al., 1984, Exp. Neurol. 126:284–290. It has been suggested as one possible explanation that "only appropriately stimulated macrophages can influence neuronal regeneration." Schwartz et al., 1994, Progress Brain Res. 103:331–341, at 338.

In fact, contrary to the teaching of the present invention, other investigators have reported that mononuclear phagocytes might exacerbate damage or limit recovery following CNS injury. Brain macrophages, when stimulated by cytokines, exhibit neurotoxic activity. Chamak et al., 1994, J. Neurosci. Res. 38:221–233. Pharmacological inhibition of mononuclear phagocyte function has been reported to promote recovery in a rabbit model of spinal cord injury. Giulian and Robertson, 1990, Annals Neurol. 27:33–42. It has been suggested that macrophage-derived cytokines may promote formation of glial scars and thereby inhibit axonal regeneration. Khan and Wigley, 1994, NeuroReport 5:1381–1385; Vick et al., 1992, J. Neurotrauma 9: S93–S103.

Citation or identification of any reference in Section 2 (or any other section) of this application shall not be construed as an admission that such reference is available as prior art to the present invention.

3. SUMMARY OF THE INVENTION

The present invention is directed to methods, and compositions, for use of allogeneic mononuclear phagocytes to promote axonal regeneration in the central nervous system of a mammal. The allogeneic mononuclear phagocytes are administered into the CNS at or near a site of injury or disease.

Allogeneic mononuclear phagocytes useful for the methods and compositions of the invention include, but are not limited to, allogeneic monocytes, macrophages and dendritic cells, and autologous monocytes, macrophages and dendritic cells.

The present invention further provides methods, and compositions, for stimulating allogeneic mononuclear phagocytes so as to enhance their capacity to promote axonal regeneration, and methods, and compositions, for use of stimulated allogeneic mononuclear phagocytes to promote axonal regeneration in the central nervous system of a mammal. The mononuclear phagocytes are stimulated by culturing them together with suitable tissue or suitable cells, or by culturing the mononuclear phagocytes in medium that has been conditioned by suitable tissue or suitable cells. Tissues suitable for this purpose include, without limitation, nerve segments, especially segments of peripheral nerve, dermis, synovial tissue, tendon sheath, liver, and other regenerating tissues. Alternatively, the mononuclear phagocytes are stimulated by culturing them in medium to which at least one suitable biologically active agent has been added. Biologically active agents suitable for this purpose include, without limitation, neuropeptides; cytokines, for instance β-interferon (IFN-β), γ-interferon (IFN-γ), tumor necrosis factor α (TNF-α), interleukin 2 (IL2), interleukin 3 (IL-3), interleukin 4 (IL-4) and monocyte chemotactic and activating factor (MCAF); colony stimulating factors, for instance macrophage colony stimulating factor (M-CSF), granulocyte-macrophage colony stimulating factor (GM-CSF) and colony stimulating factor 1 (CSF-1); neurotrophic factors, for instance neurotrophic factor 3 (NT3), nerve growth factor (NGF) and brain-derived neurotrophic factor (BDNF); and other biologically active molecules, for instance lipid A, the tripeptide fMet-Leu-Phe (fMLP), muramyl dipeptide (MDP), the ionophore A23187, and vitamin D3 binding protein. A biologically active protein or peptide may be used in its native or recombinant form.

Moreover, the present invention provides an assay for identifying additional tissues, cells and biologically active agents that are suitable for stimulating mononuclear phagocytes to enhance their capacity to promote axonal regeneration. According to this assay, mononuclear phagocytes are first cultured together with the tissue or cells to be tested, or in medium that has been conditioned by the tissue or cells to be tested or in medium to which has been added the biologically active agent to be tested. The cultured mononuclear phagocytes are then assayed for phagocytic activity, nitric oxide production, or both these activities. Mononuclear phagocytes with increased phagocytic activity, increased production of nitric oxide, or both, have an enhanced capacity to promote axonal regeneration.

4. BRIEF DESCRIPTION OF THE FIGURES

The present invention may be more fully understood by reference to the following detailed description of the invention, examples of specific embodiments of the invention and the appended figures in which:

FIG. 1 illustrates axonal regeneration in transected optic nerves of rats as detected by retrograde transport of fluorescent dye to retinal ganglion cells (RGCs). See text, Section 6, for experimental details. Shortly after transection, 2 μl of DCCM-1 medium were applied to the site of injury containing no cells (MED); $2.5 \times 10^3 - 1 \times 10^5$ non-stimulated (NS) monocytes; $2.5 \times 10^3 - 1 \times 10^5$ optic nerve-stimulated (OS) monocytes; or $2.5 \times 10^3 - 1 \times 10^5$ sciatic nerve-stimulated (SS) monocytes. Open circles represent individual experimental animals. Solid circles represent animals that showed no labeled RGCs (numbering 7, 7 and 6 in the MED, NS and OS treatment groups respectively). Horizontal lines represent the median value of each treatment group.

Figure 2:
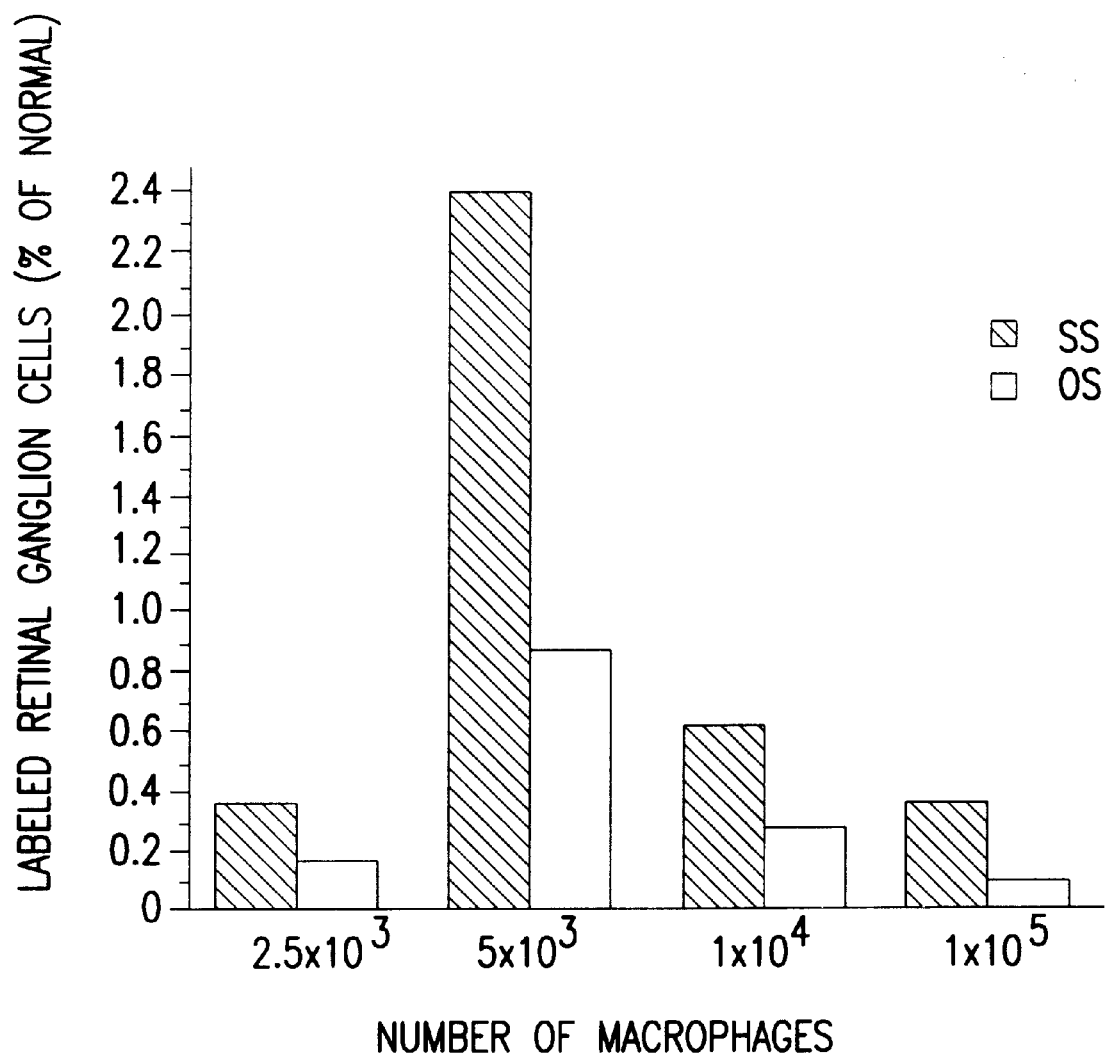
Figure 4A:
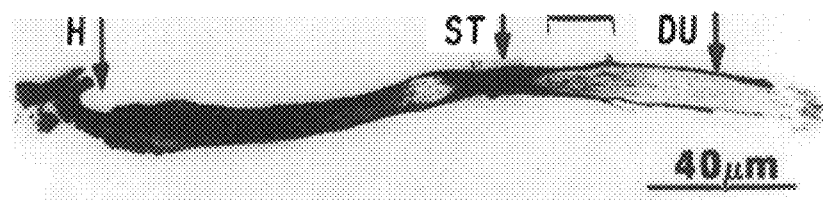
Figure 4B:
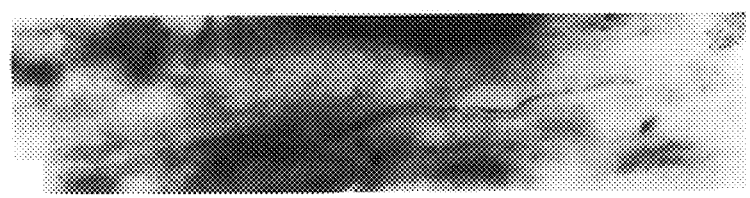
Figure 4C:
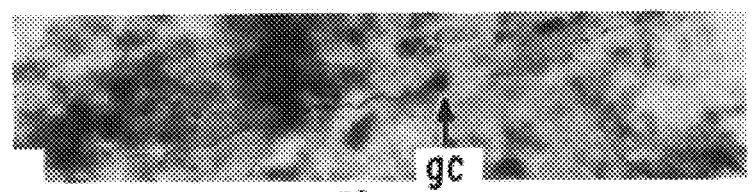
Figure 4D:
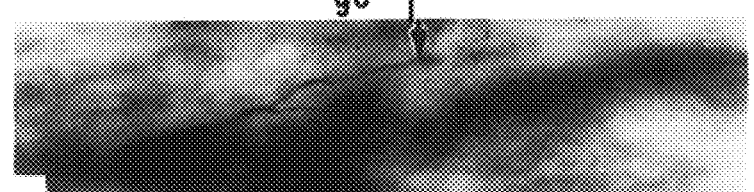
Figure 4E:
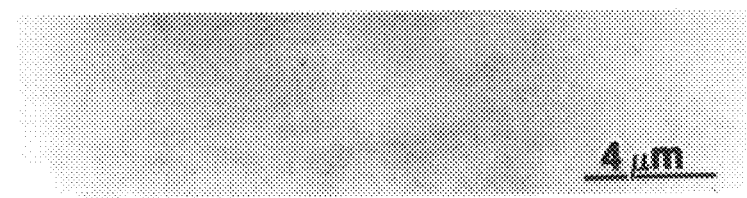

FIG. 2 illustrates axonal regeneration in transected optic nerves of rats as a function of the number and type of monocytes applied to the site of injury shortly after transection. See text, Section 6, for experimental details. At the time of transection, 2 μl DCCM-1 medium were applied to the site of injury containing optic nerve-stimulated monocytes (OS) or sciatic nerve-stimulated monocytes (SS) at a total dose of $2.5 \times 10^3$ cells; $5 \times 10^3$ cells; $10^4$ cells; or $10^5$ cells.

FIG. 3 (A–B) presents representative photomicrographs showing retrograde labeling of retinal ganglion cells in rats subjected to optic nerve transection followed by administration of (A) $5 \times 10^3$ sciatic nerve-stimulated monocytes or (B) control medium. See text, Section 6, for experimental details.

FIG. 4 (A–E) presents representative photomicrographs showing anterograde labeling of optic nerve fibers in rats subjected to optic nerve transection followed by administration of sciatic nerve-stimulated monocytes (A–D) or control medium (E). See text, Section 6, for experimental details. FIG. 4A is a low magnification view showing the point at which HRP was applied (H), the site of transection (ST) and the surrounding dura mater (DU). The bracketed region, distal to the site of transection, is shown at higher magnification in FIGS. 4B, 4C and 4D, in which growth cone-like structures (gc) are shown at the tips of the fibers.

Figure 5:
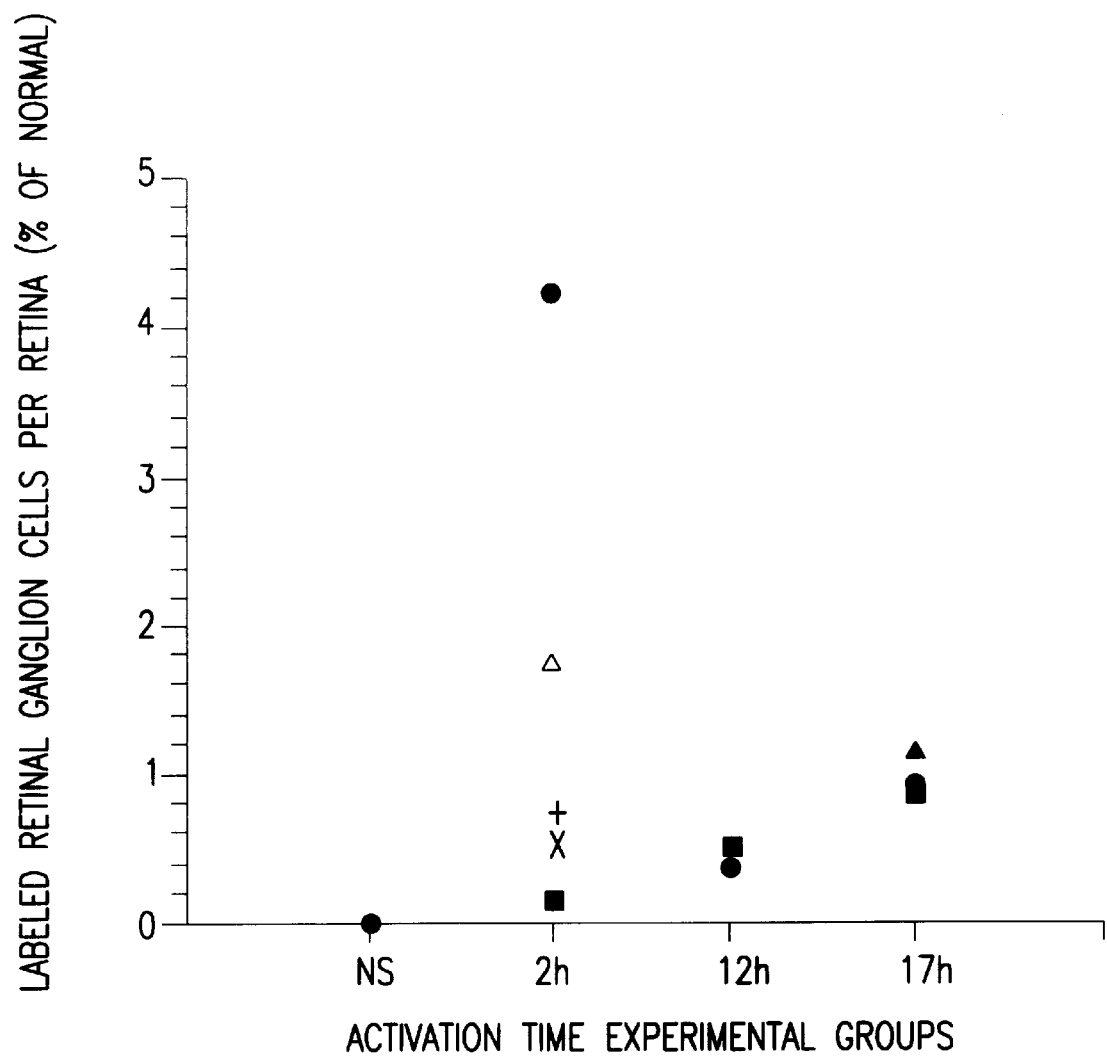

FIG. 5 illustrates axonal regeneration in transected optic nerves of rats after application to the site of injury of monocytes cultured with sciatic nerve for 2–17 hours. See text, Section 6, for experimental details. At the time of transection, 2 μl of DCCM-1 medium were applied to the site of injury containing $5 \times 10^3$ non-stimulated monocytes (NS) or $5 \times 10^3$ monocytes cultured with rat sciatic nerve for 2 hours (2 h), 12 hours (12 h) or 17 hours (17 h).

Figure 6:
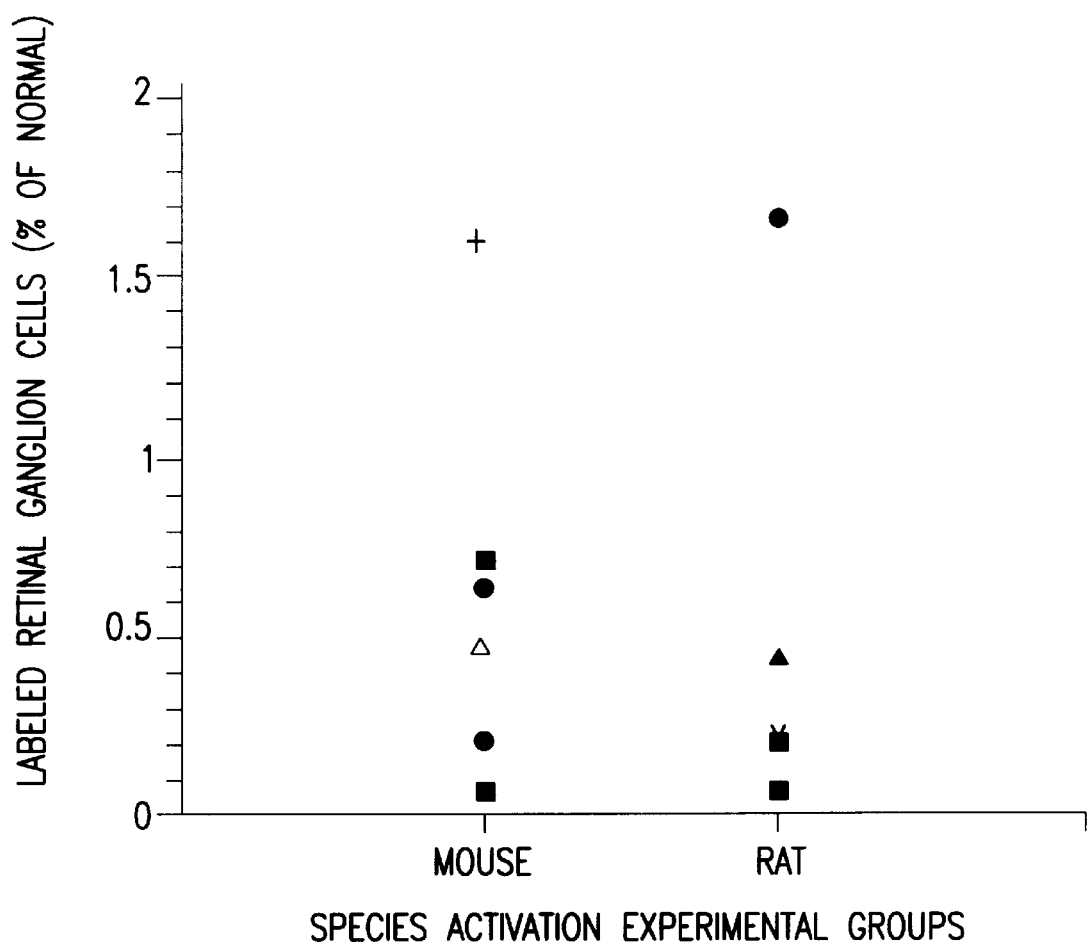

FIG. 6 illustrates axonal regeneration in transected optic nerves after administration, at the site of injury, of rat monocytes stimulated with mouse sciatic nerve or rat sciatic nerve. See text, Section 6, for experimental details. At the time of transection, 2 μl DCCM-1 medium were applied to the site of injury containing $5 \times 10^3$ monocytes cultured for 24 hours with either mouse sciatic nerve (MOUSE) or rat sciatic nerve (RAT).

Figure 7:
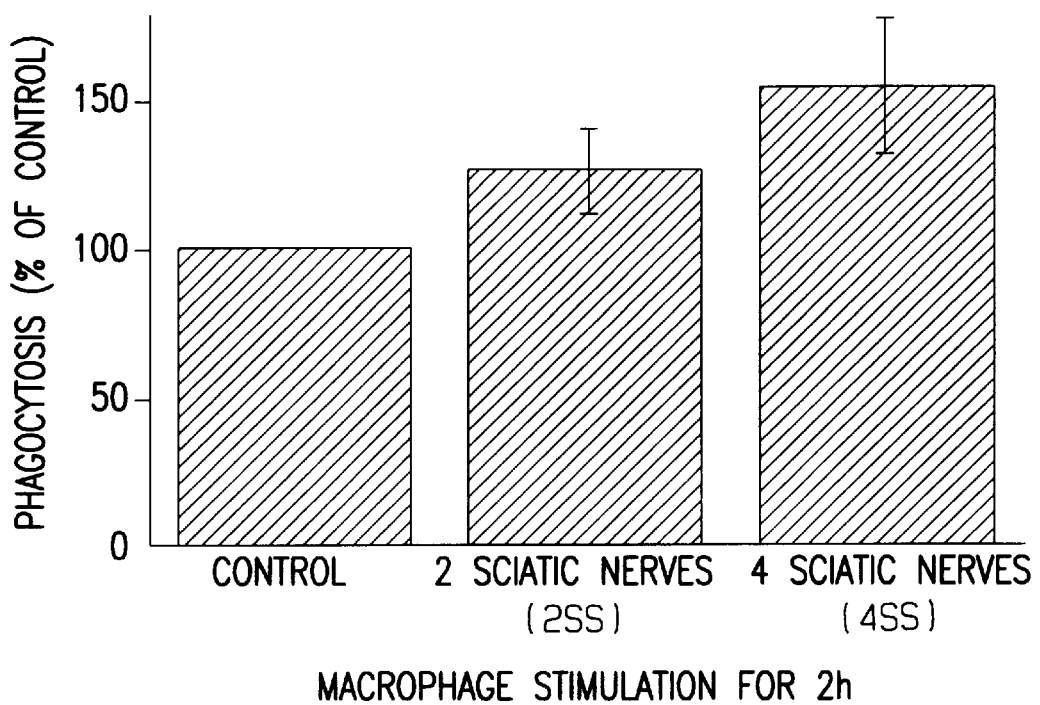

FIG. 7 illustrates the phagocytic activity of rat monocytes cultured for 2 hours with rat sciatic nerve. See text, Section 6, for experimental details. $2.5 \times 10^5$ rat monocytes were cultured in 1 ml DCCM-1 medium alone (CONTROL) or in 1 ml DCCM-1 medium with 2 segments of rat sciatic nerve (2SS) or with 4 segments of rat sciatic nerve (4SS). After 2 hours, the monocytes were exposed to fluorescent beads and cell-associated fluorescence was measured by flow cytometry.

Figure 8:
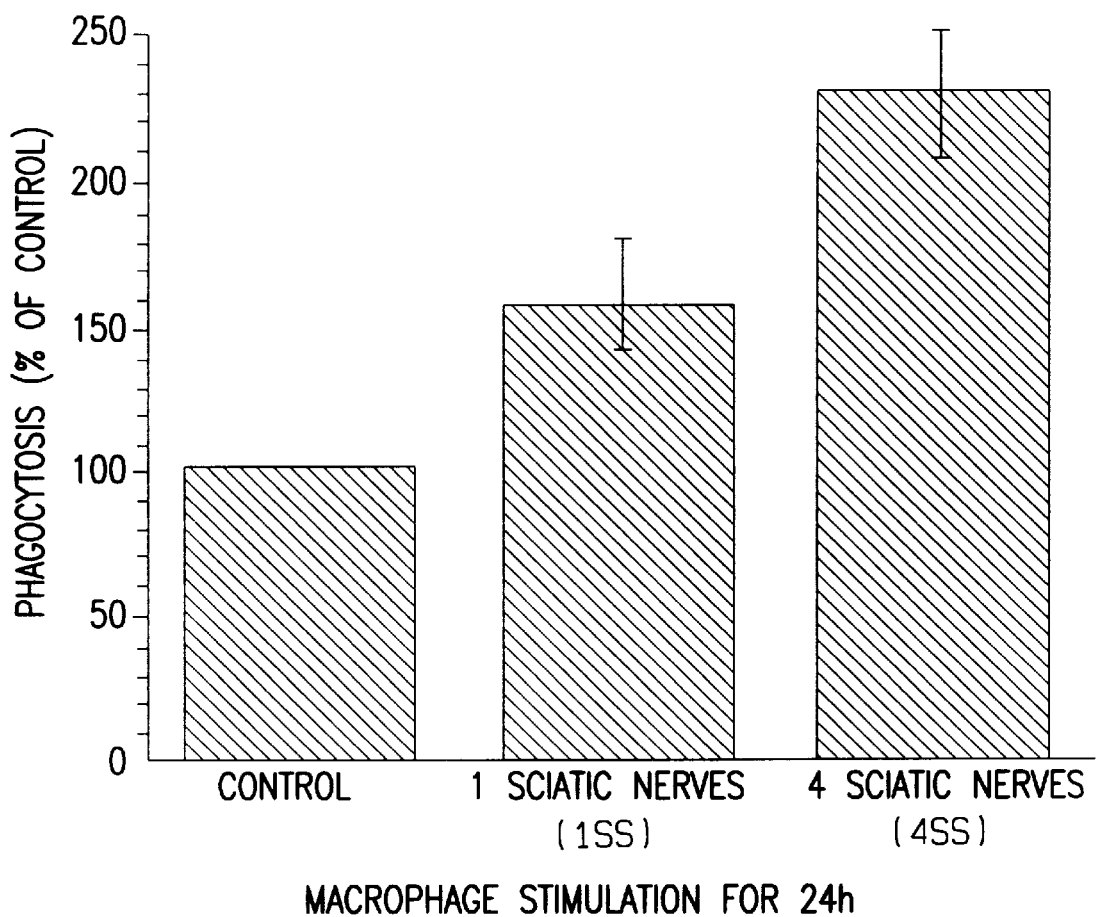

FIG. 8 illustrates the phagocytic activity of rat monocytes cultured for 24 hours with rat sciatic nerve. See text, Section 6, for experimental details. $2.5 \times 10^5$ rat monocytes were cultured in 1 ml DCCM-1 medium alone (CONTROL) or in 1 ml DCCM-1 medium with 1 segment of rat sciatic nerve (1SS) or with 4 segments of rat sciatic nerve (4SS). After 16–24 hours, the monocytes were exposed to fluorescent beads and cell-associated fluorescence was measured by flow cytometry.

Figure 9:
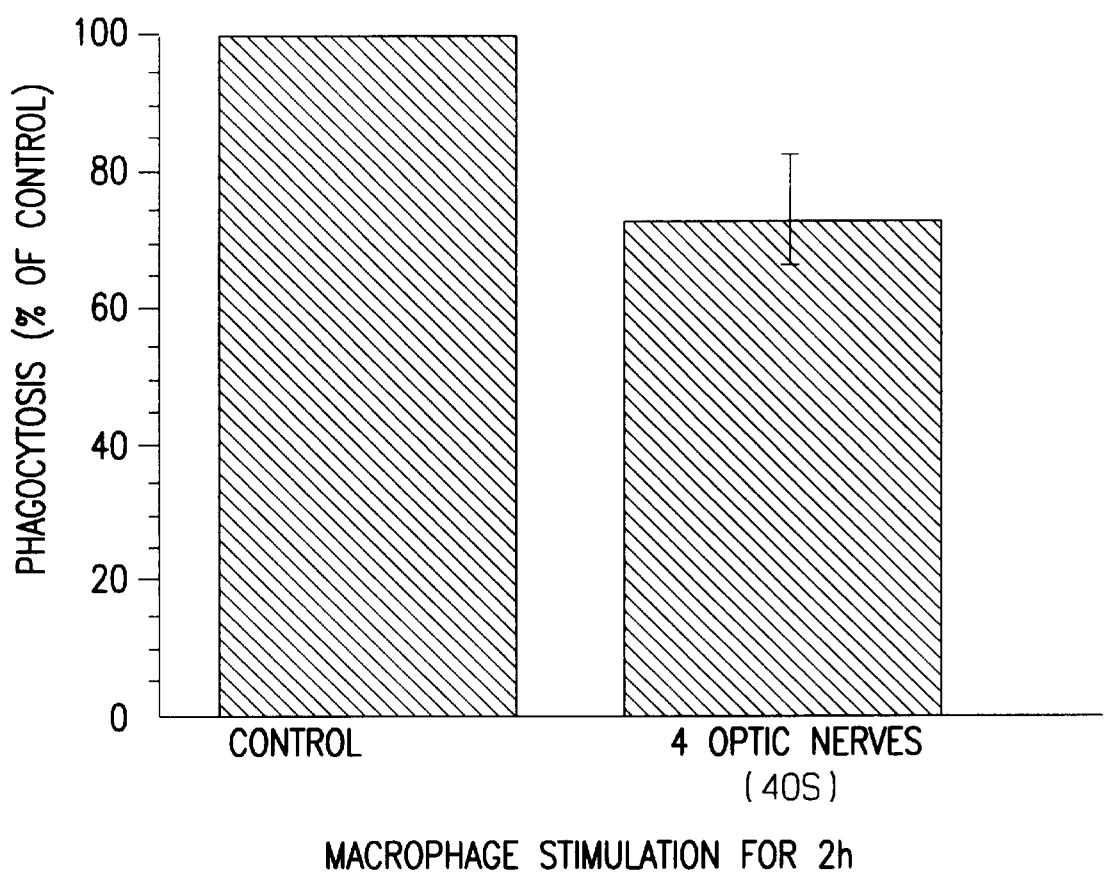

FIG. 9 illustrates the phagocytic activity of rat monocytes cultured for 2 hours with rat optic nerve. See text, Section 6, for experimental details. $2.5 \times 10^5$ rat monocytes were cultured in 1 ml DCCM-1 medium alone (CONTROL) or in 1 ml DCCM-1 medium with 4 segments of rat optic nerve (4OS). After 2 hours, the monocytes were exposed to fluorescent beads and cell-associated fluorescence was measured by flow cytometry.

Figure 10:
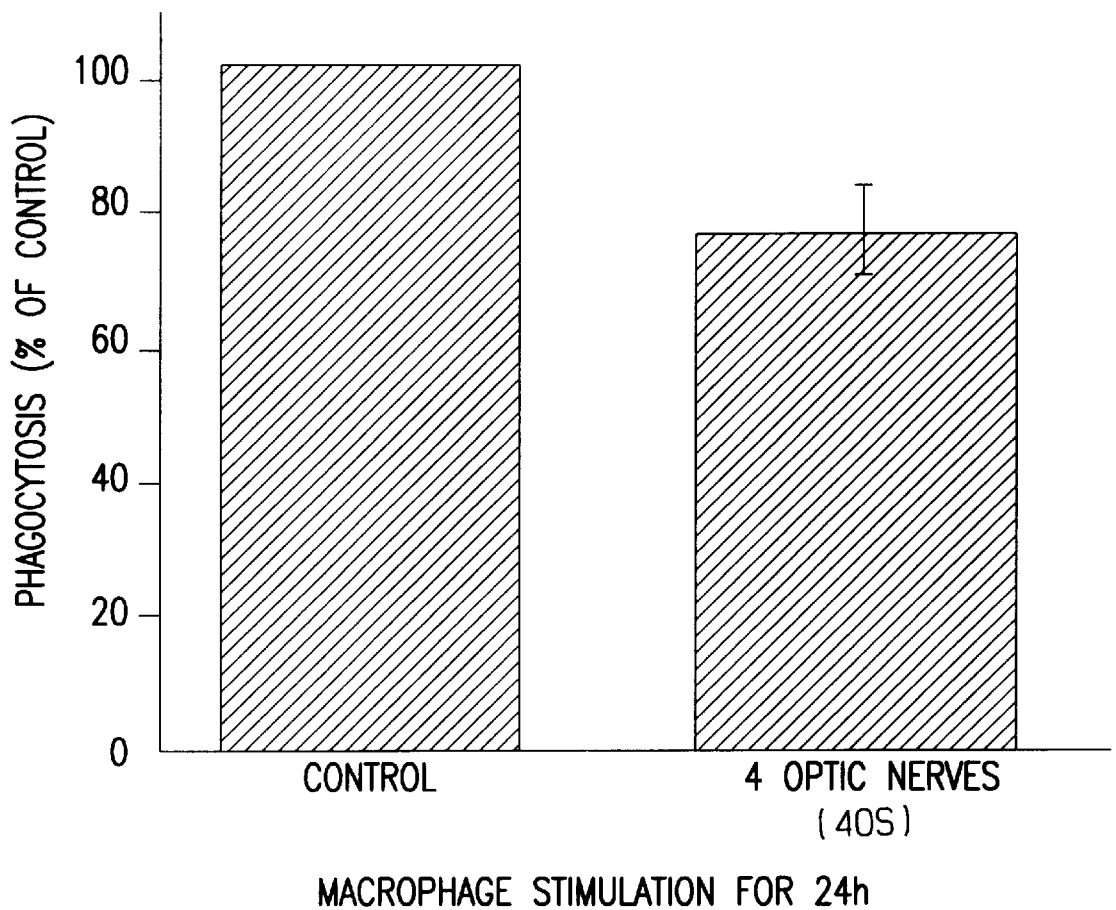

FIG. 10 illustrates the phagocytic activity of rat monocytes cultured for 24 hours with rat optic nerve. See text, Section 6, for experimental details. $2.5 \times 10^5$ rat monocytes were cultured in 1 ml DCCM-1 medium alone (CONTROL) or in 1 ml DCCM-1 medium with 4 segments of rat optic nerve (4OS). After 24 hours, the monocytes were exposed to fluorescent beads and cell-associated fluorescence was measured by flow cytometry.

Figure 11:
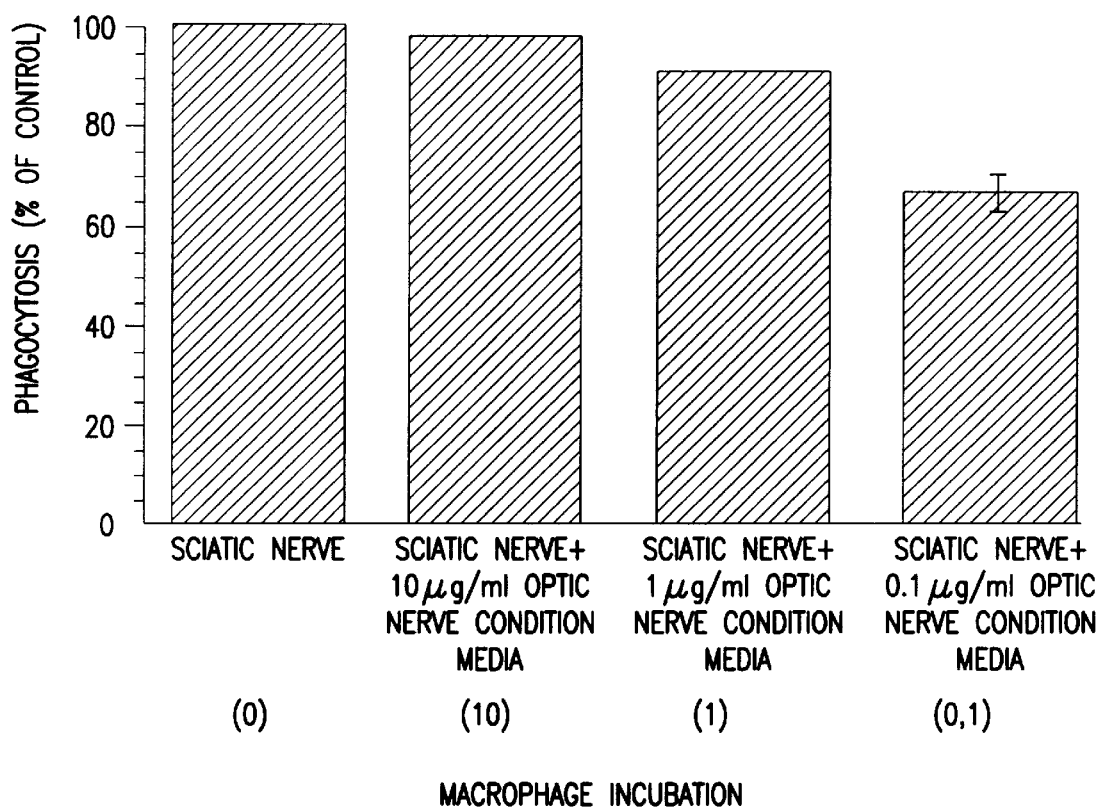

FIG. 11 illustrates the phagocytic activity of rat monocytes cultured overnight with rat sciatic nerve in the presence of medium conditioned by rat optic nerve. $5 \times 10^5$ rat monocytes were cultured in 1 ml DCCM-1 medium with 6 segments of rat sciatic nerve with no further additions (0) or with the addition of optic nerve-conditioned medium at a total protein concentration of 0.1 μg/ml (0.1), 1.0 μg/ml (1), or 10 μg/ml (10). After 24 hours, the monocytes were exposed to fluorescent beads and cell-associated fluorescence was measured by flow cytometry.

Figure 12:
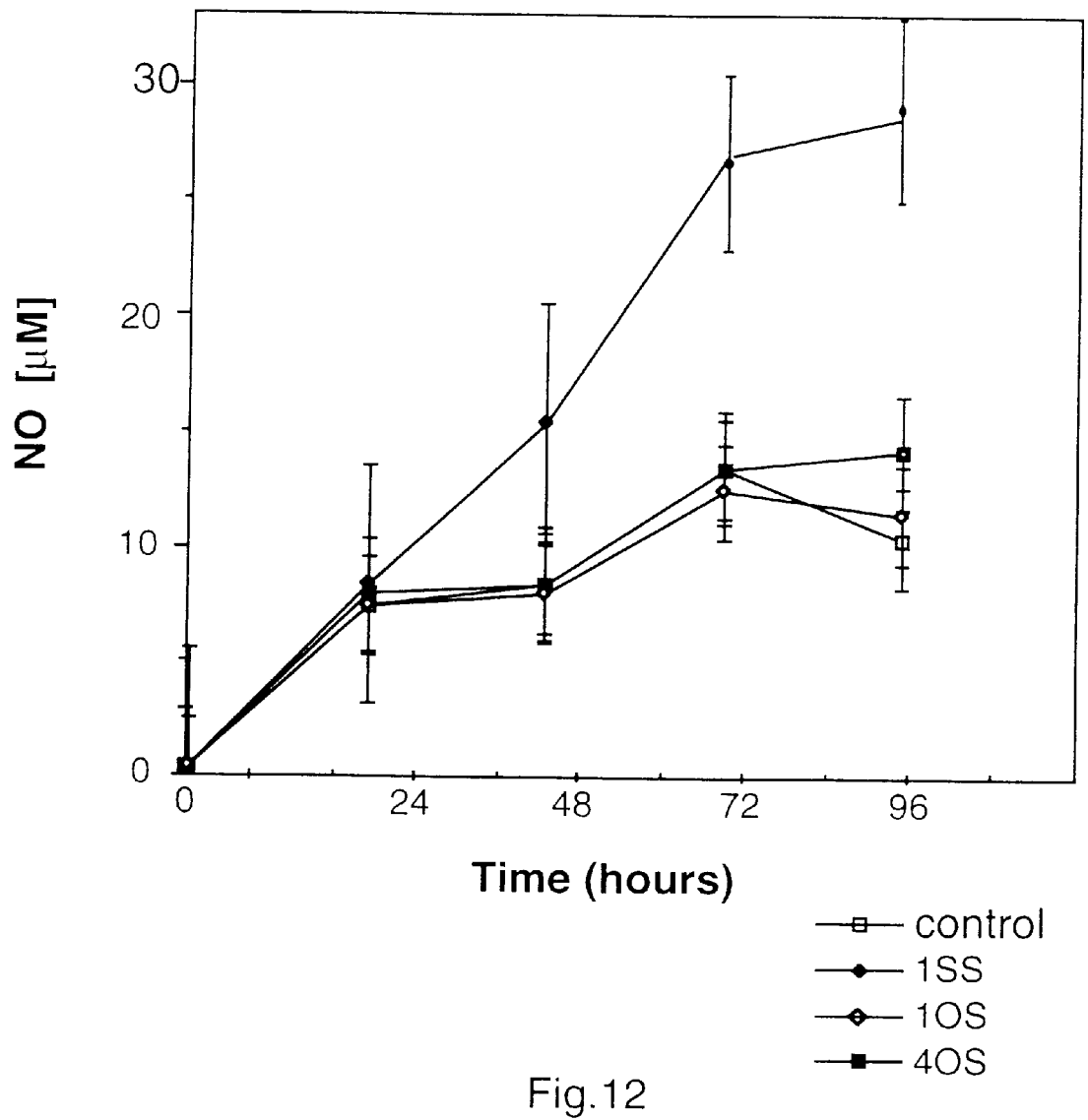

FIG. 12 illustrates nitric oxide production by rat monocytes cultured for 24, 48, 72 or 96 hours with rat sciatic nerve or with rat optic nerve. See text, Section 6, for experimental details. $10^6$ rat monocytes were cultured in 1 ml DCCM-1 medium alone (CONTROL), or in the same medium with 1 segment of rat sciatic nerve (1SS), with 1 segment of rat optic nerve (1OS), or with four segments or rat optic nerve (4OS). After 24, 48, 72 or 96 hours, the media were collected and the levels of nitric oxide were measured.

Figure 13:
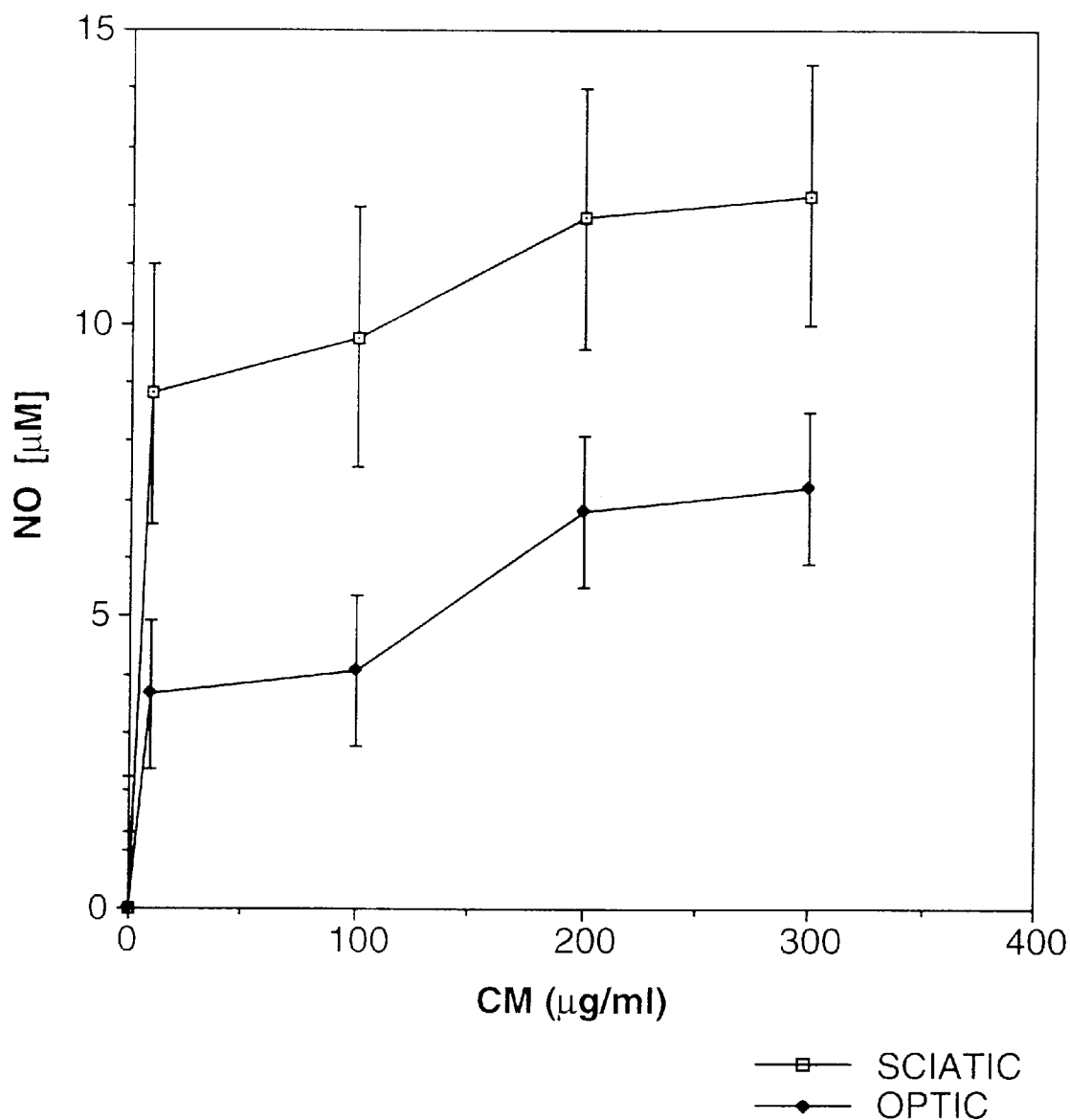

FIG. 13 illustrates nitric oxide production by rat monocytes cultured for 72 hours with medium conditioned by rat sciatic nerve or rat optic nerve. See text, Section 6, for experimental details. $10^6$ rat monocytes were cultured in 1 ml DCCM-1 medium with no further additions or with the addition of sciatic nerve-conditioned medium or optic nerve-conditioned medium at a total protein concentration of 10, 100, 200 or 300 μg/ml. After 72 hours, the media were collected and the levels of nitric oxide were measured.

Figure 14:
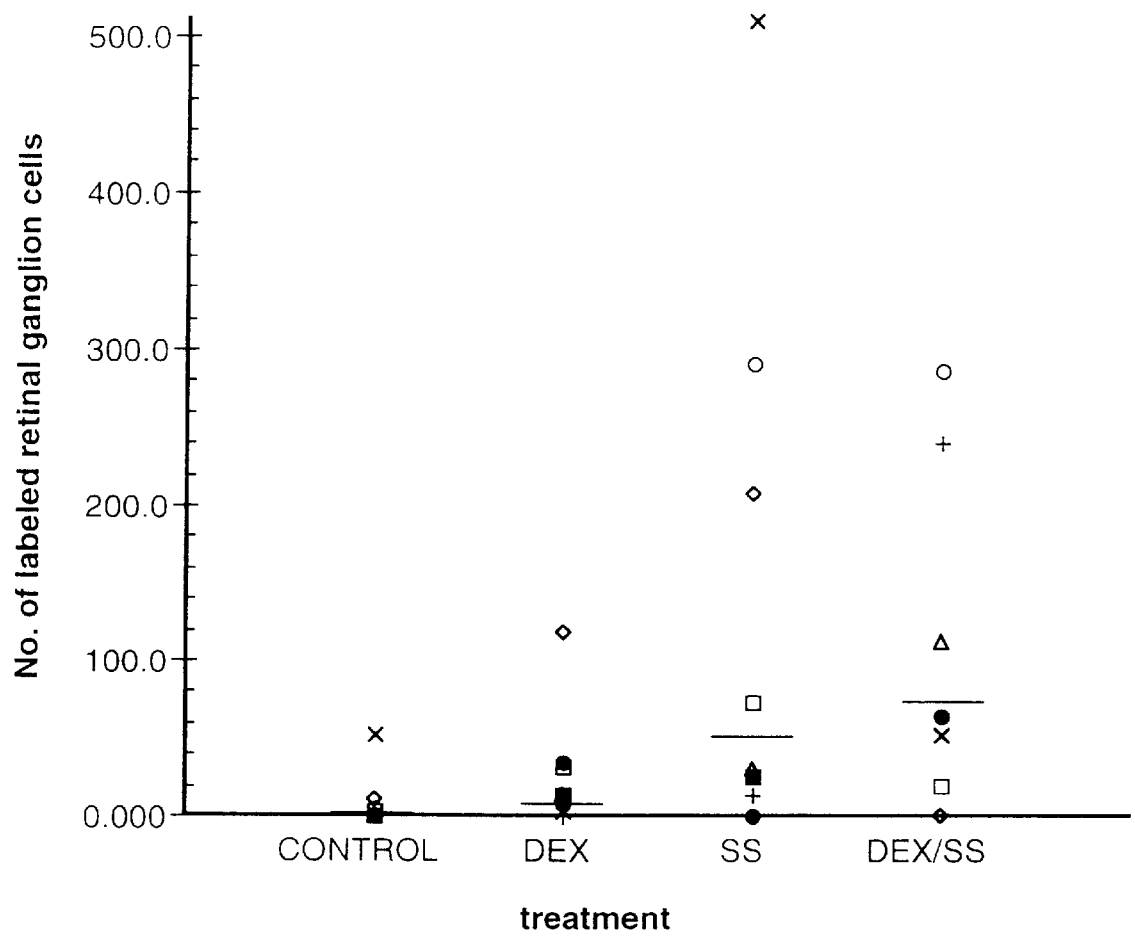

FIG. 14 illustrates axonal regeneration in transected optic nerves of rats following administration of optic nerve-stimulated monocytes combined with anti-inflammatory therapy. See text, Section 6, for experimental details. At the time of transection, 2 μl DCCM-1 medium were applied to the site of injury containing no cells or $5 \times 10^3$ sciatic nerve-stimulated rat monocytes. Concurrently, some of the rats received an intraperitoneal injection of 0.8 mg dexamethasone, producing the following treatment groups: no therapy (CONTROL), dexamethasone only (DEX), monocytes only (SS), and both dexamethasone and monocytes (DEX/SS).

5. DETAILED DESCRIPTION OF THE INVENTION

5.1 Mononuclear Phagocytes

The present invention provides methods, and compositions, for use of allogeneic mononuclear phagocytes to promote axonal regeneration following injury or disease of the central nervous system (CNS). The allogeneic mononuclear phagocytes are introduced at or near the site of CNS injury or disease.

As used herein, the term "mononuclear phagocytes" is intended to comprise, without limitation, monocytes obtained from central or peripheral blood, macrophages obtained from any site, including any tissue or cavity, macrophages derived by culturing macrophage precursors obtained from bone marrow or blood, dendritic cells obtained from any site, including spleen, lymph node, skin and lymphatic fluid, and dendritic cells derived from culturing dendritic cell precursors obtained from bone marrow or blood.

Allogeneic mononuclear phagocytes can be obtained from the circulation or from any tissue in which they reside. Peripheral blood is an easily accessible ready source of allogeneic monocytes and is used as a source according to a preferred embodiment of the invention. Especially preferred is the use of autologous monocytes purified from the peripheral blood of a subject to whom the therapeutic preparation is intended to be administered.

Allogeneic mononuclear phagocytes from other sources are well known in the art and include, without limitation, macrophages obtained from serosal cavities such as the peritoneal or pleural cavity, alveolar macrophages, and macrophages associated with other tissues, where they may be known by various terms such as Kupffer cells (in the liver) and microglial cells (in the CNS). Macrophages obtained from the CNS are suitable, as are macrophages obtained from tissues other than the CNS. Allogeneic mononuclear phagocytes further include dendritic cells, which likewise may be known by various terms, such as Langerhans cells (in the skin), veiled cells (in lymphatic fluid) and interdigitating cells (in lymph nodes). Additionally mononuclear phagocytes can be derived by culture from allogeneic brain-derived mixed glial cells or from allogeneic precursor cells, which may be obtained from bone-marrow or blood.

In a preferred embodiment, cells other than mononuclear phagocytes are depleted from the cell population to be administered. Enrichment techniques are well known to those skilled in the art and include, without limitation, elutriation; centrifugation through material of suitable density, such as a Percoll gradient (Colotta et al., 1983, J. Immunol. 132:936–944); selective adhesion on suitable surfaces followed by removal at reduced temperature or at reduced concentrations of divalent cations (Rosen and Gordon, 1987, J. Exp. Med. 166:1685–1701), mechanical removal, or removal in the presence of lidocaine; and techniques for isolating dendritic cells from blood (O'Doherty et al., 1993, J. Exp. Med. 178:1067–1078), bone marrow (Inaba et al., 1992, J. Exp. Med. 176:1693–1702) and lymphoid tissue (Macatonia et al., J. Exp. Med. 169:1255–1264). Especially preferred is a substantially purified preparation of mononuclear phagocytes.

Once the mononuclear phagocytes are obtained they may be used therapeutically at any desired time, according to the needs of the patient. The mononuclear phagocytes may, if desired, be cultured prior to administration in any suitable culture medium. Preferably, the mononuclear phagocytes are cultured in a vessel made from sterile material to which these cells show limited or no adherence. In a preferred embodiment, the mononuclear phagocytes are cultured in sterile Teflon bags prior to administration.

As used herein, "stimulated" mononuclear phagocytes are mononuclear phagocytes with an enhanced capacity to promote axonal regeneration. Preferably, the capacity of the mononuclear phagocytes to promote axonal regeneration is enhanced at least three-fold over non-stimulated mononuclear phagocytes, more preferably the capacity of the mononuclear phagocytes to promote axonal regeneration is enhanced at least 15-fold over non-stimulated mononuclear phagocytes. "Stimulatory" tissue, cells and biologically active agents are tissue, cells and biologically active agents that, when cultured together with mononuclear phagocytes, enhance the capacity of the mononuclear phagocytes to promote axonal regeneration.

In a preferred embodiment, stimulatory tissue, cells or at least one stimulatory biologically active agent is added to the culture in order to enhance the capacity of the mononuclear phagocytes to promote axonal regeneration. Preferably, one or more segments of a nerve, most preferably a peripheral nerve such as the sciatic nerve, are added to the culture. A xenogeneic nerve is suitable for this purpose or, more preferably, an allogeneic or autologous nerve. If desired, a human nerve can be obtained from any available human tissue, such as a human cadaver or a surgical specimen (e.g. an amputated limb). Alternatively other stimulatory tissue or cells are added to the culture. Dermis is suitable for this purpose and can be obtained, from a living donor or a cadaver, by punch biopsy, by surgical resection, or by any other suitable technique. Synovial tissue, tendon sheath and liver are also suitable for this purpose, as are other regenerating tissues. Additional stimulatory tissues and cells can be identified according to the assay described below. If desired, the stimulatory tissue or cells are homogenized before addition to the culture. As will be evident to those skilled in the art, the stimulatory tissue or cell homogenate can be preserved, e.g. by cryopreservation, before use.

In an alternative embodiment, at least one stimulatory biologically active agent is added to the culture in order to enhance the capacity of the mononuclear phagocytes to promote axonal regeneration. Neurotrophic factor 3 (NT3), nerve growth factor (NGF), brain-derived neurotrophic factor, β-interferon (IFN-β), γ-interferon (IFN-γ), tumor necrosis factor α (TNF-α), interleukin 2 (IL-2), interleukin 3 (IL-3), interleukin 4 (IL-4), monocyte chemotactic and activating factor (MCAF), macrophage colony stimulating factor (M-CSF), granulocyte-macrophage colony stimulating factor (GM-CSF), colony stimulating factor 1 (CSF-1), lipid A, fMet-Leu-Phe (fMLP), muramyl dipeptide (MDP), the ionophore A23187, and vitamin D3 binding protein are suitable for this purpose either singly or in combination, whether in native or recombinant form. Additional stimulatory biologically active agents (including additional stimulatory proteins and peptides) can be identified according to the assay described below.

Preferably, the mononuclear phagocytes are cultured together with stimulatory tissue, stimulatory cells, homogenate of stimulatory tissue or stimulatory cells, or at least one stimulatory biologically active agent for 24 hours. Shorter periods of culture, such as approximately 2 hours, are also effective, as are longer periods of culture, such as one or more weeks. In an alternative embodiment, stimulatory conditioned medium is prepared by incubating stimulatory tissue or cells, preferably one or more segments of a nerve, most preferably a peripheral nerve such as the sciatic nerve, in any medium that is suitable for culturing mononuclear phagocytes. After removal of the tissue or cells, mononuclear phagocytes are cultured in the stimulatory conditioned medium in order to enhance their capacity to promote axonal regeneration. After removal of the tissue or cells, the stimulatory conditioned medium can be stored and later used as desired for stimulating mononuclear phagocytes. Such stimulatory conditioned medium can be provided in the form of a commercial kit. Preferably, the stimulatory conditioned medium is preserved during storage, for instance by refrigeration, whether as a liquid or as frozen medium. Alternatively, the stimulatory conditioned medium is lyophilized.

In a preferred embodiment, the mononuclear phagocytes are exposed to a tyrosine kinase inhibitor, such as tyrphostine, before, during, or after stimulation, so as to reduce or eliminate undesired mononuclear phagocyte activities, such as secretion of TNF-α.

As will be evident to those skilled in the art, the mononuclear phagocytes can be preserved, e.g. by cryopreservation, either before or after culture.

Cryopreservation agents which can be used include but are not limited to dimethyl sulfoxide (DMSO) (Lovelock and Bishop, 1959, Nature 183:1394–1395; Ashwood-Smith, 1961, Nature 190:1204–1205), glycerol, polyvinylpyrrolidone (Rinfret, 1960, Ann. N.Y. Acad. Sci. 85:576), polyethylene glycol (Sloviter and Ravdin, 1962, Nature 196:548), albumin, dextran, sucrose, ethylene glycol, i-erythritol, D-ribitol, D-mannitol (Rowe et al., 1962, Fed. Proc. 21:157), D-sorbitol, i-inositol, D-lactose, choline chloride (Bender et al., 1960, J. Appl. Physiol. 15:520), amino acids (Phan The Tran and Bender, 1960, Exp. Cell Res. 20:651), methanol, acetamide, glycerol monoacetate (Lovelock, 1954, Biochem. J. 56:265), inorganic salts (Phan The Tran and Bender, 1960, Proc. Soc. Exp. Biol. Med. 104:388; Phan The Tran and Bender, 1961, in Radiobiology, Proceedings of the Third Australian Conference on Radiobiology, Ilbery, P.L.T., ed., Butterworth, London, p. 59), and DMSO combined with hydroxyethel starch and human serum albumin (Zaroulis and Leiderman, 1980, Cryobiology 17:311–317).

A controlled cooling rate is critical. Different cryoprotective agents (Rapatz et al., 1968, Cryobiology 5(1):18–25) and different cell types have different optimal cooling rates. See. e.g., Rowe and Rinfret, 1962, Blood 20:636; Rowe, 1966, Cryobiology 3(1):12–18; Lewis et al., 1967, Transfusion 7(1):17–32; and Mazur, 1970, Science 168:939–949 for effects of cooling velocity on survival of marrow-stem cells and on their transplantation potential. The heat of fusion phase where water turns to ice should be minimal. The cooling procedure can be carried out by use of, e.g., a programmable freezing device or a methanol bath procedure.

Programmable freezing apparatuses allow determination of optimal cooling rates and facilitate standard reproducible cooling. Programmable controlled-rate freezers such as Cryomed or Planar permit tuning of the freezing regimen to the desired cooling rate curve.

After thorough freezing, cells can be rapidly transferred to a long-term cryogenic storage vessel. In one embodiment, samples can be cryogenically stored in mechanical freezers, such as freezers that maintain a temperature of about −80° C. or about −20° C. In a preferred embodiment, samples can be cryogenically stored in liquid nitrogen (−196° C.) or its vapor. Such storage is greatly facilitated by the availability of highly efficient liquid nitrogen refrigerators, which resemble large Thermos containers with an extremely low vacuum and internal super insulation, such that heat leakage and nitrogen losses are kept to an absolute minimum.

Considerations and procedures for the manipulation, cryopreservation, and long term storage of hematopoietic stem cells, particularly from bone marrow or peripheral blood, are largely applicable to the mononuclear phagocytes of the invention. Such a discussion can be found, for example, in the following references, incorporated by reference herein: Gorin, 1986, Clinics in Haematology 15(1): 19–48; Bone-Marrow Conservation, Culture and Transplantation, Proceedings of a Panel, Moscow, Jul. 22–26, 1968, International Atomic Energy Agency, Vienna, pp. 107–186.

Other methods of cryopreservation of viable cells, or modifications thereof, are available and envisioned for use, e.g., cold metal-mirror techniques. See Livesey and Linner, 1987, Nature 327:255; Linner et al., 1986, J. Histochem. Cytochem. 34(9):1123–1135; see also U.S. Pat. No. 4,199,022 by Senken et al., U.S. Pat. No. 3,753,357 by Schwartz, U.S. Pat. No. 4,559,298 by Fahy.

Frozen cells are preferably thawed quickly (e.g., in a water bath maintained at 37–41° C.) and chilled immediately upon thawing. It may be desirable to treat the cells in order to prevent cellular clumping upon thawing. To prevent clumping, various procedures can be used, including but not limited to the addition before and/or after freezing of DNAse (Spitzer et al., 1980, Cancer 45:3075–3085), low molecular weight dextran and citrate, hydroxyethyl starch (Stiff et al., 1983, Cryobiology 20:17–24), or acid citrate dextrose (Zaroulis and Leiderman, 1980, Cryobiology 17:311–317), etc.

The cryoprotective agent, if toxic in humans, should be removed prior to therapeutic use of the thawed mononuclear phagocytes. One way in which to remove the cryoprotective agent is by dilution to an insignificant concentration.

Once frozen mononuclear phagocytes have been thawed and recovered, they are used to promote axonal regeneration as described herein with respect to non-frozen mononuclear phagocytes.

5.2 Methods of Use

According to the present invention, the mononuclear phagocytes are suspended in a sterile pharmaceutically acceptable carrier and administered into the CNS of a mammal, including a human subject, at or near a site of injury or disease. Optionally, treatment with mononuclear phagocytes may be combined with local or systemic anti-inflammatory therapy, for instance administration of a steroid such dexamethosone or methylprednisolone, or administration of a non-steroidal anti-inflammatory agent. The present invention contemplates the optional use of a steroid or non-steroidal anti-inflammatory agent at any dose that is effective in the subject to be treated. Such effective doses are well known to those skilled in the art and include, for example, standard-dose therapy, such as systemic methylprednisolone 100 mg daily for a human adult, and high-dose therapy, such as systemic methylprednisolone 1000 mg daily for a human adult.

In a preferred embodiment, the pharmaceutically acceptable carrier is PBS or a culture medium. However, alternative pharmaceutically acceptable carriers will readily be apparent to those skilled in the art.

In a preferred embodiment, the mononuclear phagocytes are administered immediately following CNS injury and are introduced at the site of CNS injury, for example with a glass micropipette. However, the present invention encompasses administration of mononuclear phagocytes at any time following CNS injury or disease and encompasses introduction of the mononuclear phagocytes at or near a site of CNS injury or disease by any neurosurgically suitable technique.

The compositions and methods of the present invention are useful for treating any injury or disease of the CNS that results in or is accompanied by axonal damage. The injury or disease may be situated in any portion of the CNS, including the brain, spinal cord, or optic nerve. One example of such injury or disease is trauma, including coup or countercoup injury, penetrating trauma, and trauma sustained during a neurosurgical operation or other procedure. Another example of such injury or disease is stroke, including hemorrhagic stroke and ischemic stroke. Yet another example of such injury or disease is optic nerve injury accompanying optic neuropathy or glaucoma. Still further examples of CNS injury or disease will be evident to those skilled in the art from this description and are encompassed by the present invention. The compositions and methods of the present invention are useful for treating CNS injury or disease that results in axonal damage whether or not the subject also suffers from other disease of the central or peripheral nervous system, such as neurological disease of genetic, metabolic, toxic, nutritional, infective or autoimmune origin.

The optimal dose of mononuclear phagocytes is proportional to the number of nerve fibers affected by CNS injury or disease at the site being treated. In a preferred embodiment, the dose ranges from about $2.5 \times 10^3$ to about $10^5$ mononuclear phagocytes for treating a lesion affecting about $10^5$ nerve fibers, such as a complete transection of a rat optic nerve, and ranges from about $2.5 \times 10^4$ to about $10^6$ mononuclear phagocytes for treating a lesion affecting about $10^6$ nerve fibers, such as a complete transection of a human optic nerve. More preferably, the dose ranges from about $2.5 \times 10^3$ to about $5 \times 10^4$ mononuclear phagocytes for treating a lesion affecting about $10^5$ nerve fibers and ranges from about $2.5 \times 10^4$ mononuclear phagocytes to about $5 \times 10^5$ mononuclear phagocytes for treating a lesion affecting about $10^6$ nerve fibers. Especially preferred is a dose of about $5 \times 10^3$ mononuclear phagocytes for treating a lesion affecting about $10^5$ nerve fibers and a dose of about $5 \times 10^4$ mononuclear phagocytes for treating a lesion affecting about $10^6$ nerve fibers.

5.3 Assay for Stimulatory Tissues, Cells and Biologically Active Agents

The present invention provides an assay for identifying stimulatory tissues and cells and stimulatory biologically active agents. Mononuclear phagocytes are cultured together with the tissue or cells to be tested, in medium conditioned by the tissue or cells to be tested, or in medium to which the biologically active agent or agents to be tested have been added at various concentrations. Thereafter, the mononuclear phagocytes are assayed for phagocytic activity, or nitric oxide production. Mononuclear phagocytes with increased phagocytic activity or increased production of nitric oxide have an enhanced capacity to promote axonal regeneration. In a preferred embodiment, both phagocytic activity and nitric oxide production are measured, and mononuclear phagocyte stimulation is detected by observing an increase in either of these activities, more preferably in both of these activities.

Preferably, the phagocytic capacity of the mononuclear phagocytes is increased by at least 10 percent, more preferably by at least 25 percent, still more preferably by at least 50 percent. Preferably, the nitric oxide production of the mononuclear phagocytes is increased by at least 50 percent, more preferably by at least 100 percent, and still more preferably by at least 200 percent.

In one embodiment, phagocytic activity is measured by contacting the mononuclear phagocytes with labeled particles and subsequently determining the amount of label associated with the cells. A wide variety of particles can be used for this purpose, including without limitation latex or polystyrene beads and naturally occurring cells, such as red blood cells, yeast and bacteria. optionally, the particles can be opsonized, for instance with immunoglobulin or complement. The particles can be labeled with any suitable marker, including without limitation a fluorescent marker (such as fluorescein or rhodamine), a radioactive marker (such as a radioactive isotope of iodine, carbon or hydrogen), and an enzyme. Alternatively, the assay can be performed with unlabeled particles (e.g. red blood cells or yeast); the unlabeled particles are detected by any suitable method, such as microscopically, with or without staining. In a preferred embodiment, the mononuclear phagocytes are first contacted with fluorescent polystyrene beads; cell-associated fluorescence is subsequently measured by flow cytometry.

In one embodiment, nitric oxide production is measured by the Griess-reagent assay as described in Hibbs et al., 1987, Science 235:473–476, which is incorporated herein by reference. However, other assays for nitric oxide production may be used, as are known to those of skill in the art. See, e.g., Packer (ed.), 1996, Methods in Enzymology 268:58–247, which is incorporated herein by reference.

The assay of the present invention also provides a means of determining the period of culture required in order to stimulate the mononuclear phagocytes. Mononuclear phagocytes are cultured for various periods with stimulatory tissue or cells, in medium conditioned by stimulatory tissue or cells, or in medium to which at least one stimulatory biologically active agent has been added. Thereafter, the phagocytic activity or nitric oxide production of the mononuclear phagocytes, or both these properties, are measured.

A period of culture sufficient to increase the phagocytic activity of the mononuclear phagocytes by at least 10 percent, preferably by at least 25 percent, more preferably by at least 50 percent, or sufficient to increase the nitric oxide production of the mononuclear phagocytes by at least 50 percent, preferably by at least 100 percent, more preferably by at least 200 percent, is sufficient to stimulate their capacity to enhance axonal regeneration.

The following examples are presented for purposes of illustration only and are not intended to limit the scope of the invention in any way.

6. EXAMPLE: USE OF MONOCYTES TO PROMOTE AXONAL REGENERATION

6.1 Material and Methods

6.1.1 Isolation and Culture of Monocytes

Peripheral blood was pooled from adult Sprague-Dawley (SPD) rats. Monocytes were isolated by fractionation on a one-step Percoll gradient as previously described. F. Colotta et al., 1984, J. Immunol. 132:936–944. The monocyte-enriched fraction was recovered from the Percoll interface, washed once with PBS to remove traces of Percoll, and resuspended at $1 \times 10^6$ cells/ml in DCCM-1 medium (Beit Ha'emek Ltd., Kibbutz Beit Ha'emek, Israel). The cells were cultured in Teflon bags at 37° C. as previously described, Andreesen et al., 1983, J. Immunolog. Meth. 56:295–304, with 5% $CO_2$, as is conventional in the art. Usually, each bag received 10 ml containing $1 \times 10^7$ cells. For measurement of phagocytic activity or nitric oxide production, monocytes from SPD or Wistar rats were used, and were cultured in polypropylene tubes or in Teflon bags.

6.1.2 Stimulation of Monocytes

Non-stimulated monocytes (NS) were prepared by culturing isolated monocytes in a Teflon bag or polypropylene tubes, as described above, for 2–24 hours. Sciatic nerve-stimulated monocytes (SS) were prepared by culturing monocytes in a Teflon bag or polypropylene tubes for 2–24 hours together with at least one segment of a rat sciatic nerve. Optic nerve-stimulated monocytes (OS) were prepared by culturing monocytes in a Teflon bag or polypropylene tubes for 2–24 hours together with at least one segment of a rat optic nerve. Each nerve segment was 1.0–1.5 cm long in experiments 6.2.1 and 6.2.2, and was 0.5–1.0 cm long in experiments 6.2.3 to 6.2.9; a constant ratio of 1 nerve segment to $5 \times 10^6$ cultured monocytes was used, except where otherwise noted.

After 2–24 hours in culture, monocytes were centrifuged for 3 minutes at 1000×g, washed once with phosphate buffered saline (PBS), and resuspended in DCCM-1 medium at $1.25 \times 10^6 – 5 \times 10^6$ cells/ml. The monocytes were 95% pure as determined by morphology and by immunocytochemistry with the monoclonal antibody ED1 (Serotec, Oxford, England) as described. Hirschberg et al., 1994, J. Neuroimmunol. 50:9–16.

6.1.3 Optic Nerve Transection

Anesthetized adult SPD rats, 8–9 weeks old, average mass 300 grams, were subjected to optic nerve transection as described. Eitan et al., 1994, Science 264:1764–1768. The left optic nerve was exposed through a small opening in the meninges. A curved glass dissector with a 200 μm tip and a smooth blunt edge was moved across the nerve to create a complete transection 2–3 mm distal to the optic globe, taking care not to damage the peripheral blood vessels. As used herein, the term "distal" means away from the optic globe and towards the brain. Shortly after transection, 2 μl of medium containing cultured monocytes or 2 μl of medium alone were introduced at the site of injury by means of a curved glass micropipette with a 25 μm lumen. The meningeal opening was made about 200 μm from the site of transection, in order to minimize leakage of cells from the site of application. In some experiments, dexamethasone (0.8 mg/rat) was administered by intraperitoneal injection to some of the rats shortly after transection.

6.1.4 Assays for Axonal Regeneration

6.1.4.1 Retrograde Labeling of Axons

Seven to eight weeks following transection, the lipophilic neurotracer dye, 4-(4-(didecylamino)styryl)-N-methylpyridinium iodide (4Di-10ASP) (Molecular Probes, Eugene, Oregon, USA) was applied to the injured optic nerve, 2 mm distal to the site of injury. One week after application of the dye, the retina was removed, prepared as a flattened whole mount in 4% paraformaldehyde solution, and examined by fluorescence microscopy to detect and count the number of labeled retinal ganglion cells (RGCs) in the entire retina. Only axons that had regrown past the site of injury to the site at which dye was applied could take up the dye and transport it retrogradely to the retinal ganglion cells.

When applied to rat optic nerves that have not previously been transected, this procedure labels an average of 21,623 RGCs per retina. The results for optic nerves that were subjected to transection are expressed as a percentage of this standard, to control for the efficiency of the 4Di-10ASP labeling technique.

6.1.4.2 Anterograde Labeling of Axons

Seven to eight weeks following transection, a fresh incision was made in the previously transected optic nerve 1 mm proximal to the site of transection. As used herein, "proximal" means towards the optic globe and away from the brain. Horseradish peroxidase (HRP) (type VI-A, Sigma, Tel Aviv, Israel) was introduced through the incision by means of a sterile swab soaked in a 50% (w/v) solution of HRP in PBS. Eight to twelve hours after application of the HRP, the rats were perfused through the carotid artery with PBS followed by 4% paraformaldehyde in PBS as a fixative. The optic nerves were excised, 50 μm longitudinal cryosections were taken and processed for visualization of HRP activity using diaminobenzidine and cobalt intensification as described. Lavie et al., 1992, Brain Res. 575:1–5.

6.1.5 Assay of Pragocytic Activity

Monocytes from SPD or Wistar rats were suspended in DCCM-1 medium ($2.5 \times 10^5$ or $5 \times 10^5$ cells in 1 ml) and were cultured without further additions or together with the indicated number of syngeneic rat sciatic or optic nerve segments or with the addition of medium conditioned by syngeneic rat optic nerve at the indicated concentrations of total protein. See Section 4 for details. To assay phagocytic activity, a working solution of fluorescent noncarboxylated microspheres ("FLUORESBRITE"™, Polysciences, Warrington, Pennsylvania, USA, Catalog. No. 17152) was prepared by diluting 1 drop of a stock solution in 10 ml DCCM-1 medium and adding this working solution to the monocyte suspension at a further dilution of 1:100, after removing the nerve segments. After three hours at 37° C., the cells were washed once with DCCM-1 medium or with phosphate-buffered saline, and cell-associated fluorescence was measured by flow cytometry (FACS). In some experiments, 1 ml ice-cold PBS was added prior to the washing step, to halt phagocytosis.

6.1.6 Assay of Hitric Oxide Production

Monocytes from SPD or Wistar rats were suspended in DCCM-1 medium ($10^6$ cells in 1 ml) and were cultured without further additions or with the indicated number of syngeneic rat sciatic or optic nerve segments or with the addition of medium conditioned by syngeneic rat sciatic or optic nerve at the indicated concentrations of total protein. See Section 4 for details. After the indicated time in culture, the nerve segments (if any) were removed, the samples were centrifuged, and the supernatants were collected. To assay nitric oxide production, 100 $\mu$l aliquots of supernatant were incubated with 100 $\mu$l of Griess reagent (1% sulfanilamide, 10% N-(1-naphthyl)-ethylene diamine hydrochloride in 2.5% $H_3PO_4$) at room temperature for 10 minutes. Colorimetry was performed at 550 nm with an ELISA reader and the amount of nitric oxide calculated according to a reference curve using sodium nitrite (Sigma, Israel) as standard. The reaction medium (DCCM-1) was used as a blank. In control experiments, optic and sciatic nerve segments were found to produce negligible amounts of nitric oxide.

6.2 Results 6.2.1 Promotion of Axonal Regeneration by Stimulated and Non-Stimulated Monocytes Rats were subjected to optic nerve transection and treated at the time of injury with control medium or with $2.5 \times 10^3$–$1 \times 10^5$ non-stimulated (NS) monocytes, $2.5 \times 10^3$–$1 \times 10^5$ sciatic nerve-stimulated (SS) monocytes, or $2.5 \times 10^3$–$1 \times 10^5$ optic nerve-stimulated (OS) monocytes.

The number of labeled retinal ganglion cells (RGCs) in rats from each treatment group is shown in FIG. 1 as a percentage of RGCs labeled in normal optic nerves. Rats receiving no cells showed almost no labeling of RGCs. Rats receiving NS monocytes showed labeling of modest numbers of RGCs, while treatment with OS monocytes resulted in labeling of greater numbers of RGCs. In rats receiving SS monocytes, the median number of labeled RGCs was over 5-fold higher than in the rats treated with OS monocytes, and was about 15-fold higher than in the rats treated with NS monocytes.

6.2.2 Axonal Regeneration after Treatment with Various Doses of Sciatic Nerve- or Optic Nerve-Stimulated Monocytes To study regeneration as a function of the dose of monocytes administered, rats were subjected to optic nerve transection and treated at the time of injury with OS monocytes or SS monocytes at a total dose of $2.5 \times 10^3$; $5 \times 10^3$; $1 \times 10^4$; or $1 \times 10^5$ cells.

The average number of labeled retinal RGCs in each treatment group is shown in FIG. 2 as a percentage of RGCs labeled in normal optic nerves. RGC labeling was highest after treatment with $5 \times 10^3$ SS monocytes. Higher or lower doses of SS monocytes promoted axonal regeneration but were less effective. Treatment with OS monocytes similarly promoted axonal regeneration, though less effectively. The peak effect, with both OS and SS monocytes, occurred at a dose of $5 \times 10^3$ monocytes; at higher or lower doses the beneficial effect on axonal regeneration was less marked.

Representative fluorescence micrographs of labeled RGCs in retinas after treatment with SS monocytes or control medium are shown in FIG. 3. The absence of labeled RGCs following treatment with control medium indicates that transection was complete and that the labeled RGCs represent regenerating axons that traversed the site of transection and not merely fibers that escaped the experimental injury.

The photomicrographs in FIG. 4 further verify that regrowth has occurred. In nerves treated with control medium (E) no labeled fibers could be seen distal to the site of HRP application. In nerves treated with SS monocytes (A–D) labeled fibers were seen emerging from the proximal part of the nerve, crossing the site of transection (ST) and extending distally. Structures resembling growth cones (gc) were observed at the tips of these labeled fibers.

6.2.3 Axonal Regeneration After Treatment with Monocytes Stimulated with Rat Sciatic Nerve Segments for Various Intervals To study the capacity of monocytes to promote axonal regeneration after stimulation for various intervals with sciatic nerve segments, rats were subjected to optic nerve injury and treated at the time of injury with $5 \times 10^3$ monocytes cultured with rat sciatic nerve segments for two hours (2 h), twelve hours (12 h) or seventeen hours (17 h). The number of labeled RGCs in individual rats from each treatment group is shown in FIG. 5 as a percentage of RGCs labeled in normal optic nerves. Monocytes showed an enhanced capacity to promote axonal regeneration after culture with sciatic nerve segments for each interval tested.

6.2.4 Axonal Regeneration After Treatment with Monocytes Stimulated with Rat or Mouse Sciatic Nerve Segments To compare the ability of sciatic nerve segments derived from rat and mouse to stimulate the capacity of monocytes to promote axonal regeneration, rats were subjected to optic nerve transection and treated at the time of injury with $5 \times 10^3$ rat monocytes cultured for 24 hours either with 1–8 segments of rat sciatic nerve (RAT) or with 2–16 segments of mouse sciatic nerve (MOUSE). The number of labeled RGCs in individual rats from each treatment group is shown in FIG. 6 as a percentage of RGCs labeled in normal optic nerves. Both rat and mouse sciatic nerve stimulated the capacity of monocytes to promote axonal regeneration.

6.2.5 Phagocytic Activity of Monocytes following Culture with Segments of Rat Sciatic Nerve Rat monocytes were suspended at $2.5 \times 10^5$ cells in 1 ml DCCM-1 medium and were cultured for 2–24 hours without further additions (CONTROL), with 1 segment of rat sciatic nerve (1SS), with 2 segments of rat sciatic nerve (2SS), or with 4 segments of rat sciatic nerve (4SS).

The phagocytic activity of the 2SS and 4 SS preparations after 2 hours in culture is shown in FIG. 7 relative to the phagocytic activity of CONTROL monocytes. After culture for 2 hours with two segments of sciatic nerve, the monocytes showed increased phagocytic activity; after culture for 2 hours with four segments of sciatic nerve, the monocytes showed a greater increase in phagocytic activity.

The phagocytic activity of the 1SS and 4SS preparations after 24 hours in culture is shown in FIG. 8 relative to the phagocytic activity of CONTROL monocytes. After culture for 24 hours with one segment of sciatic nerve, the monocytes showed increased phagocytic activity; after culture for 24 hours with four segments of sciatic nerve, the increase in phagocytic activity was even greater. The 4SS preparation showed a greater increase in phagocytic activity after 24 hours than after 2 hours.

Addition of sciatic nerve-conditioned medium to the monocyte culture likewise increased the phagocytic activity of the monocytes (data not shown).

6.2.6 Phagocytuc Activity of Monocytes following Culture with Segments of Rat Optic Nerve Rat monocytes were suspended at $2.5 \times 10^5$ cells in 1 ml DCCM-1 medium and were cultured for 2–24 hours without further additions (CONTROL) or with 4 segments of rat optic nerve (4OS). The phagocytic activity of the 4OS preparations after 2 hours in culture is shown in FIG. 9 relative to the phagocytic activity of CONTROL monocytes. After culture for 2 hours with four segments of optic nerve, the monocytes showed a decrease in phagocytic activity.

The phagocytic activity of the 4OS preparations after 24 hours in culture is shown in FIG. 10 relative to the phagocytic activity of CONTROL monocytes. After culture for 24 hours with four segments of optic nerve, the monocytes showed a decrease in phagocytic activity similar to that seen after 2 hours.

6.2.7 Phagocytic Activity of Monocytes following Culture with Sciatic Nerve Segments in the Presence of Optic Nerve-Conditioned Medium Optic nerve conditioned medium was prepared by culturing 10 segments of rat optic nerve for 2 hours in 1 ml DCCM-1 medium. While fresh DCCM-1 medium is protein-free, the optic nerve conditioned medium contained protein. Rat monocytes were suspended at $2.5 \times 10^5$ cells in 1 ml DCCM-1 medium and were cultured for 24 hours with 1–6 segments of rat sciatic nerve without further additions (0) or with optic nerve conditioned medium at a total protein concentration of 10 µg/ml (10), 1 µg/ml (1) or 0.1 µg/ml (0.1).

FIG. 11 presents the phagocytic activity of monocytes cultured with sciatic nerve in the presence of optic nerve conditioned medium relative to the phagocytic activity of monocytes cultured with sciatic nerve in the absence of optic nerve conditioned medium. Addition of optic nerve conditioned medium attenuated the enhancement in phagocytic activity caused by culture with sciatic nerve. This attenuation was most marked in the preparation that received 0.1 µg/ml optic nerve conditioned medium. Similar results (not shown) were obtained when optic nerve segments were cultured in DCCM-1 medium for 8 hours and the resulting supernatants were dialyzed overnight at 4° C. against PBS and subsequently stored at −20° C. or −70° C.

6.2.8 Nitric Oxide Production of Monocytes Cultured with Sciatic Nerve, Optic Nerve, or Conditioned Medium Rat monocytes were suspended at $10^6$ cells in 1 ml DCCM-1 medium and were cultured for 24–96 hours without further additions (CONTROL), with 1 segment of rat sciatic nerve (1SS), or with 4 segments of rat optic nerve (4OS). The nitric oxide production of these preparations is shown in FIG. 12. Monocytes cultured with sciatic nerve showed significantly increased production of nitric oxide, whereas optic nerve had no significant effect.

FIG. 13 illustrates nitric oxide production of monocytes cultured for 72 hours with medium conditioned by rat sciatic nerve or rat optic nerve. Sciatic nerve-conditioned medium produced a statistically significant increase in nitric oxide production, whereas optic nerve-conditioned medium had no statistically significant effect. This result demonstrates that stimulation of mononuclear phagocytes by sciatic nerve is mediated by one or more soluble factors.

6.2.9 Axonal Regeneration after Treatment with Sciatic Nerve-Stimulated Monocytes Combined with Anti-Inflammatory Therapy To study whether anti-inflammatory therapy prevents monocyte-mediated axonal regeneration, rats were subjected to optic nerve transection. Control medium or sciatic nerve-stimulated monocytes were administered at the transection site shortly after injury, either without additional therapy or together with intraperitoneal administration of dexamethasone. Eight weeks later, axonal regeneration was measured by retrograde labeling. As shown in FIG. 14, rats receiving no therapy (CONTROL) or dexamethasone only (DEX) shown negligible regrowth, whereas sciatic nerve-stimulated monocytes promoted axonal regeneration, whether given alone (SS) or concurrently with intraperitoneal dexamethasone (DEX/SS).

6.3 Discussion

These examples demonstrate that monocytes administered at a site of CNS injury promoted axonal regeneration. All monocytes tested were effective at promoting axonal regeneration. However, monocytes were stimulated (i.e., showed an enhanced capacity to promote axonal regeneration) by culture with a nerve segment, especially with a segment of a peripheral nerve, e.g. sciatic nerve from rat or mouse. This stimulation was evident after all periods of culture tested, i.e. from 2–24 hours. For treating a total transection of a rat optic nerve, which contains about $10^5$ nerve fibers, optimal results were obtained by administering about $5 \times 10^3$ monocytes. However, every dose tested showed a beneficial effect on axonal regeneration.

These examples also demonstrate that monocytes show increased phagocytic activity and increased nitric oxide production after culture with one or more segments of sciatic nerve or in sciatic nerve-conditioned medium. Thus, measurement of phagocytic activity, nitric oxide production or both these properties provides a rapid and efficient method of screening tissues and cells for their capacity to stimulate monocytes to promote axonal regeneration.

The present invention is not to be limited in scope by the exemplified embodiments, which are intended as illustrations of single aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A pharmaceutical composition comprising:
   (a) mammalian mononuclear phagocytes that have been cultured with at least one nerve segment or with medium conditioned by at least one nerve segment; and
   (b) a pharmaceutically acceptable carrier, wherein said nerve segment is a segment of a peripheral nerve or an optic nerve.

2. The pharmaceutical composition according to claim 1, in which said nerve segment is a segment of a peripheral nerve.

3. The pharmaceutical composition according to claim 2, in which said mammalian mononuclear phagocytes are human mononuclear phagocytes.

4. The pharmaceutical composition according to claim 3, in which said human mononuclear phagocytes are human monocytes.

5. The pharmaceutical composition according to claim 2, comprising a population of mammalian mononuclear phagocytes that has been enriched by depletion of cells other than mononuclear phagocytes.

6. The pharmaceutical composition according to claim 2, in which said mononuclear phagocytes are suspended in a pharmaceutically acceptable fluid.

7. The pharmaceutical composition according to claim 2, in which said mononuclear phagocytes are monocytes, macrophages obtained from a serosal cavity, alveolar macrophages, macrophages obtained from the liver, or macrophages derived from culturing macrophage precursors obtained from bone marrow or from blood.

8. A pharmaceutical composition comprising:
   (a) mammalian mononuclear phagocytes that have been cultured together with stimulatory tissue other than nerve segments or with medium conditioned by stimulatory tissue other than nerve segments; and
   (b) a pharmaceutically acceptable carrer.

9. The pharmaceutical composition according to claim 8, in which said mammalian mononuclear phagocytes have been cultured together with dermis or with medium conditioned by dermis.

10. A pharmaceutical composition comprising:
    (a) mammalian mononuclear phagocytes that have been cultured together with a plurality of stimulatory tissues or with medium conditioned by a plurality of stimulatory tissues; and (b) a pharmaceutically acceptable carrier.

11. A pharmaceutical composition comprising:

(a) human mononuclear phagocytes that have been cultured together with stimulatory cells or with medium conditioned by stimulatory cells; and (b) a pharmaceutically acceptable fluid in which said mononuclear phayocytes are suspended.

12. The pharmaceutical composition according to claim 8, 9 or 10, in which said mammalian mononuclear phagocytes are human mononuclear phagocytes.

13. The pharmaceutical composition according to claim 12, in which said human mononuclear phagocytes are human monocytes.

14. The pharmaceutical composition according to claim 8, 9 or 10, in which said mononuclear phagocytes are human mononuclear phagocytes that are suspended in a pharmaceutically acceptable fluid.

15. The pharmaceutical composition according to claim 14, in which said human mononuclear phagocytes are human monocytes.

16. The pharmaceutical composition according to claim 8, 9 or 10, comprising a population of mammalian mononuclear phagocytes that has been enriched by depletion of cells other than mononuclear phagocytes.

17. The pharmaceutical composition according to claim 16, in which said mammalian mononuclear phagocytes are human mononuclear phagocytes.

18. The pharmaceutical composition according to claim 17, in which said human mononuclear phagocytes are human monocytes.

19. The pharmaceutical composition according to claim 1 or 8, in which said mononuclear phagocytes are monocytes, macrophages obtained from a serosal cavity, alveolar macrophages, macrophages obtained from the liver, or macrophages derived from culturing macrophage precursors obtained from bone marrow or from blood.

20. The pharmaceutical composition according to claim 1 or 8, in which said mononuclear phagocytes are not microglial cells.

21. The pharmaceutical composition according to claim 8 or 11, comprising a population of mammalian mononuclear phagocytes that has been enriched by depletion of cells other than mononuclear phagocytes.

22. The pharmaceutical composition according to claim 11, wherein said mononuclear phagocytes are monocytes.

* * * * *